United States Patent [19]

Yeh et al.

[11] Patent Number: 5,679,338
[45] Date of Patent: Oct. 21, 1997

[54] USE OF IL-4 FOR INHIBITION OF THE BREAKDOWN OF ARTICULAR CARTILAGE AND OTHER TISSUES

[75] Inventors: Li-an Yeh, Shrewsbury; Andrew J. Augustine, Boston; Adrian Sheldon, Watertown, all of Mass.

[73] Assignee: Osteoarthritis Science, Inc., Cambridge, Mass.

[21] Appl. No.: 242,011

[22] Filed: May 12, 1994

[51] Int. Cl.$^6$ .......................... A61K 38/20; C07K 14/00
[52] U.S. Cl. ................... 424/85.2; 424/85.1; 514/12; 514/825
[58] Field of Search ........................ 424/85.2, 85.1; 514/12, 825; 530/351

[56] References Cited

U.S. PATENT DOCUMENTS

| 5,188,827 | 2/1993 | Black | 424/85.2 |
|---|---|---|---|
| 5,206,345 | 4/1993 | Masinovsky et al. | |
| 5,236,705 | 8/1993 | Hamilton et al. | 424/85.2 |
| 5,246,700 | 9/1993 | Yamaguchi et al. | 424/85.2 |
| 5,382,427 | 1/1995 | Plunkett et al. | 424/85.2 |

FOREIGN PATENT DOCUMENTS

| 490006 | 6/1992 | European Pat. Off. | A61K 37/02 |
|---|---|---|---|
| WO9107186 | 5/1991 | WIPO | A61K 37/02 |
| WO9204044 | 3/1992 | WIPO | |
| WO9205805 | 4/1992 | WIPO | |

OTHER PUBLICATIONS van Roon et al: Inhibiton of RA synovial fliuid mononuclear cell-induced cartliage damage by interleukin-4. Arthritis & Rheumatism, vol. 36 (supplement), 1993, p. s154 (abstract number B78).

Interleukin Receptor—Targeted Molecules for Treatment of Inflammatory Arthritis, CA118(5):329-36F.

IL-4 and Interleukin-1 Beta synergistically induced VCAM-1 CA116(21):212855W.

Synergistic anti-inflammatory compositions containing interleukin-4, CAA115(6):166651f.

Interleukin-4 in method and compostions for degradation and prevention of fibrin deposits associated with pathological conditions, CA114(3):22375a.

Zlotnik, A. et al., Evidence for effects of IL-4 (B cell Stimulatory Factor 1) on macrophages: Enhancement of Antigen Presenting Ability of Bone Marrow Deried Macrophages, J. Immunol., 138:4275-4279 (1987).

Primary Examiner—Ponnathapura Achutamurthy
Attorney, Agent, or Firm—Fish & Richardson P.C.

[57] ABSTRACT

Applicants' invention discloses therapeutic compositions and methods for treating articular cartilage breakdown associated with osteoarthritis and rheumatoid arthritis. The compositions comprise a therapeutically effective amount of IL-4 to reduce or inhibit breakdown of articular cartilage, optionally in the presence of a pharmaceutically acceptable carrier or excipient. Methods for treating articular cartilage breakdown comprise administering a therapeutically effective amount of IL-4 to reduce or inhibit breakdown of articular cartilage, optionally in the presence of a pharmaceutically acceptable carrier to a subject in need of such treatment. The invention also relates to compositions and methods for treating tumor metastases, periodontal disease, emphysema and osteoporosis.

2 Claims, 7 Drawing Sheets

USE OF IL-4 FOR INHIBITION OF THE BREAKDOWN OF ARTICULAR CARTILAGE AND OTHER TISSUES

The invention relates to therapeutic compositions and methods for the inhibition of articular cartilage breakdown associated with osteoarthritis. The present invention also relates to compositions and methods for the inhibition of tumor metastases, emphysema, osteoporosis and periodontal disease. The compositions comprise interleukin-4 (IL-4), optionally in the presence of a pharmaceutically acceptable carrier or excipient. Methods for the inhibition of articular cartilage breakdown comprise administering to a subject having osteoarthritis a therapeutically effective amount of IL-4 to inhibit articular cartilage breakdown. Methods for the inhibition of tumor metastases, emphysema, osteoporosis and periodontal disease comprise administering to a subject a therapeutically effective amount of IL-4 to inhibit these diseases.

Osteoarthritis is a disorder of articular cartilage and subchondral bone. Osteoarthritis is the most common form of all articular disorders and first appears asymptomatically in the second to third decade of life and becomes universal by age 70. Osteoarthritis is manifested in nearly all vertebrates.

In contrast to other arthritic disorders, osteoarthritis is not characterized by extreme inflammation. Inflammation is commonly associated with disease states such as rheumatoid arthritis, and it is generally thought to be caused by the action of cytokines such as interleukin-1 (IL-1), and tumor necrosis factor-$\alpha$ (TNF-$\alpha$), histamine and prostaglandin $E_2$ ($PGE_2$).

Articular cartilage is found on the articulating (joint) surface at the end of long bones. The cortical shell of compact bone (subchondral bone) is covered by a thin layer of articular cartilage, which is a specialized form of hyaline cartilage.

The most probable initial event in osteoarthritis is mitosis of the chondrocyte with increased synthesis of the proteoglycans (PG) and type II collagen, the principal structural elements of cartilage. The earliest triggering event is a decrease in concentration of PG in the immediate neighborhood of the chondrocyte. The second event is increased synthesis of bone by osteoblasts in the subchondral bone, presumably by intercellular communication between chondrocyte and osteoblast in the subchondral bone cells. The third event is metaplasia of the peripheral synovial cells resulting in formation of osteochondrophytes (the tissue is not only bone but a mixture of connective tissues with a coating of fibrocartilage and sometimes islands of hyaline cartilage on the surface) around the periphery of the joint. The degree of formation of these "spurs" varies from joint to joint and in some proportion to underlying causative mechanisms. The fourth event is the formation of bony cysts in the marrow below the subchondral bone. The mechanism is that of extrusion of joint fluid through the hyaline cartilage clefts into the marrow with a fibroblastic, osteoblastic cellular reaction around the synovial fluid.

Initially, osteoarthritis is noninflammatory and onset is subtle and gradual, usually involving one to only a few joints. As the disease progresses, joint motion becomes diminished, flexion contractures occur, tenderness and crepitus or grading sensations appear.

Other examples of conditions which result from collagen and PG breakdown are tumor metastases, osteoporosis, emphysema, and periodontal disease.

IL-4 is a known substance and has been cloned by Severison, et al. from cDNA prepared from a ConA-stimulated mouse T cell line. The mouse IL-4 is a protein consisting of 120 amino acids. The structure of human IL-4 has also been determined by Yokota, et al., which is a protein consisting of 129 amino acids. It has been reported that both of the mouse and human IL-4 contain two sugar chain-binding sites.

IL-4 is a 20 kD glycoprotein and is a B cell growth and differentiation factor and is also the product of activated T lymphocytes and has a variety of stimulatory effects on B cells, T cells and mast cells. IL-4 has been used to treat disorders related to diseases of the immune and other systems. For example, IL-4 has been used to inhibit IL-2-induced proliferation of B-cell malignancies. Banchereau, et al., EP 490,006. IL-4 has been cloned and expressed and its effect on enhancing the antigen presenting ability of bone marrow derived macrophages has been disclosed. Zlotnik, A. et al. J. of Immunology, 138:4275–4279 (1987). Also, compositions comprising tumor necrosis factor and IL-4 have been used for inhibition of human breast cancer, vulvar carcinoma and histiocytic lymphoma. Aggarwal, et al. PCT WO 92/05805. It has also been found that systemic use of IL-4 from *E. coli* inhibits solid tumor growth of epithelial and connective tissues. Plunkett, et al., PCT WO 92/04044.

IL-4 is known to have the following physiological activities, (1) it induces DNA synthesis of B-lymphocytes activated by an antigen or an anti-IgM antibody, and promotes the growth of B-lymphocytes; (2) it selectively differentiates B cells stimulated by LPS to IgG1-producing cells so as to reduce the production of IgG3, it also promotes the production of IgE; (3) it induces the expression of class II major histocompatibility antigen (Ia antigen); (4) it promotes growth of T cells and mastocytes; (5) it promotes growth and differentiation of thymus cells; (6) it expresses the Fce receptor; and (7) it promotes growth of hematopoietic stem cells.

IL-4 has been demonstrated to suppress the synthesis of IL-1, TNF-$\alpha$ and $PGE_2$ in human monocytes, Hart, P. H., et al., Proc. Natl. Acad. Sci. USA, 86:3803–3807 (1989). IL-4 has also shown an augmentation effect of glucocorticoid on human monocytes. Hart, P. H. et al., Lymphokine Research, 9:147–153 (1990). IL-4 has further been found to suppress the biosynthesis of interstitial collagenase and 92 kD gelatinase in human alveolar macrophages, Lacraz, S., et al., J. Clin. Invest., 90:382–388 (1992). IL-4 has also been found to inhibit bone resorption. Watanabe, K., et al., Biochem. Biophys. Res. Comm., 172:1035–1041 (1990).

However, it has not been known heretofore that IL-4 can be employed to prevent collagen and PG breakdown in articular cartilage.

In accordance with one aspect of the present invention there is provided a method for reducing or inhibiting articular cartilage breakdown, which is eventually manifested as osteoarthritis, which comprises administering to a subject in need of such treatment a therapeutically effective amount of IL-4 to reduce or inhibit articular cartilage breakdown.

In accordance with another aspect of the present invention there is provided a composition for reducing or inhibiting articular cartilage breakdown which comprises a therapeutically effective amount of IL-4 to reduce or inhibit articular cartilage breakdown.

In accordance with yet a further aspect of the present invention, there are provided compositions and methods for treating metastatic cancer, emphysema and bone diseases such as periodontal disease and osteoporosis, which comprise administering to a subject having need of such treatment, a therapeutically effective amount of IL-4 to reduce or eliminate tissue breakdown associated with these diseases, optionally in the presence of a pharmaceutically acceptable carrier or excipient.

These and other aspects of the present invention should be apparent to those skilled in the art from the teachings herein.

BRIEF DESCRIPTION OF DRAWINGS

The following drawings are illustrative of embodiments of the present invention and are not meant to limit the scope of the invention as encompassed by the claims.

In accordance with one aspect of the invention there is provided a method for reducing or inhibiting collagen and PG breakdown in articular cartilage, which, if untreated, leads to osteoarthritis, which comprises administering to a subject a therapeutically effective amount of IL-4 to reduce or inhibit the collagen and PG breakdown in articular cartilage.

Reference to IL-4 is to be taken as reference to principally the human lymphokine IL-4, as described, for example, in International Patent Application No. WO 87/02990 which is incorporated herein in its entirety by reference. IL-4 also refers, however, to animal IL-4 as produced for example by mice, rats, horses, cats, dogs, cows and sheep. The definition IL-4 includes all proteins, polypeptides and peptides which are natural or recombinant IL-4's or derivatives thereof having IL-4 activity in the treatment of diseases associated with tissue breakdown. IL-4 derivatives are generally substitution, insertion or deletion variants of IL-4, wherein one or more amino acids are substituted, inserted or deleted from the native IL-4 amino acid sequence. The IL-4's used in the processes and compositions of this invention may be produced by purification from natural sources using conventional techniques or may be produced by recombinant DNA technology. Generally, IL-4 used in this invention is homogeneous or substantially homogeneous, that is at least 95% and more preferably 99% pure as ascertained by, for example, polyacrylamide gel electrophoresis (PAGE) and high performance liquid chromatography (HPLC).

Collagen and PG are ubiquitous in various tissues of the body and add to the stability and structure of those tissues. Collagen, for example, is an albumenlike substance which is found in muscle, bone and cartilage and is the substance upon which tissue cells are built. Collagen and PG comprise the majority of articular cartilage. Collagen and PG breakdown can occur due to the actions of the cytokines, IL-1 and TNF-α, and also the action of LPS. IL-1, TNF-α and LPS either act alone to break down collagen and PG or IL-1 and TNF-α act in combination to provide a synergistic effect to break down collagen and PG in a more efficient manner than they would alone. Cytokines, including IL-4 and TNF-α, further act to stimulate the production and release of metalloproteinases in vivo which further act to enzymatically degrade collagen and PG. Examples of metalloproteinases include collagenase, stromelysin and gelatinase.

While Applicant will not limit the scientific reasoning of the present invention to any particular theory, Applicant has found that IL-4 inhibits the breakdown of collagen and PG in articular cartilage and other tissues which is induced by IL-1, TNF-α and LPS alone and the combination of IL-1 and TNF-α. The inhibition of IL-1 and TNFα by IL-4 also prevents the production and release of metalloproteinases in vivo. IL-4 may be used to treat this breakdown which encompasses both preventing such breakdown and reducing or eliminating such breakdown once it commences.

Figure 1A:
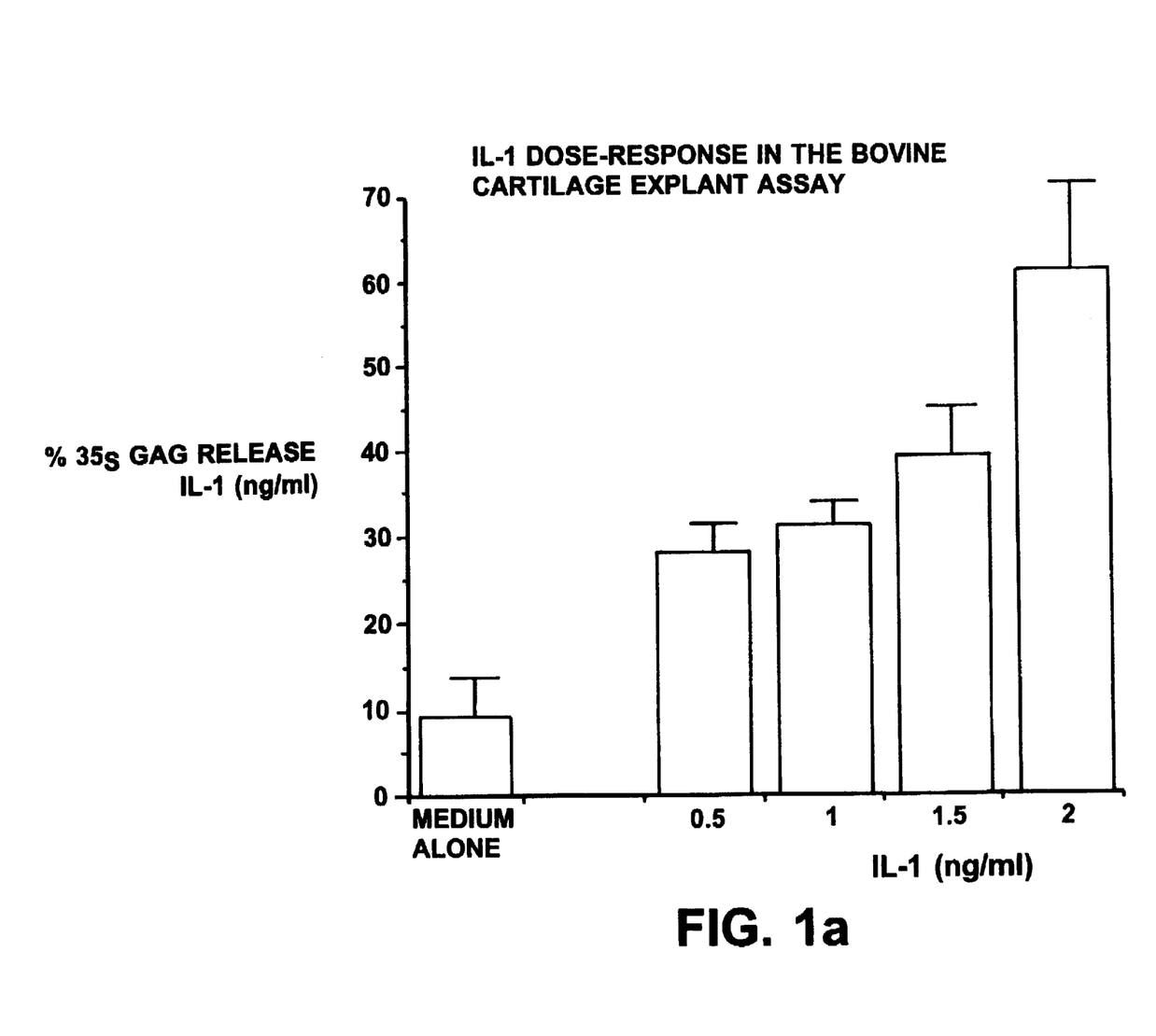
FIG. 1a describes the IL-1 increased PG breakdown in the cartilage explant system.
Figure 1B:
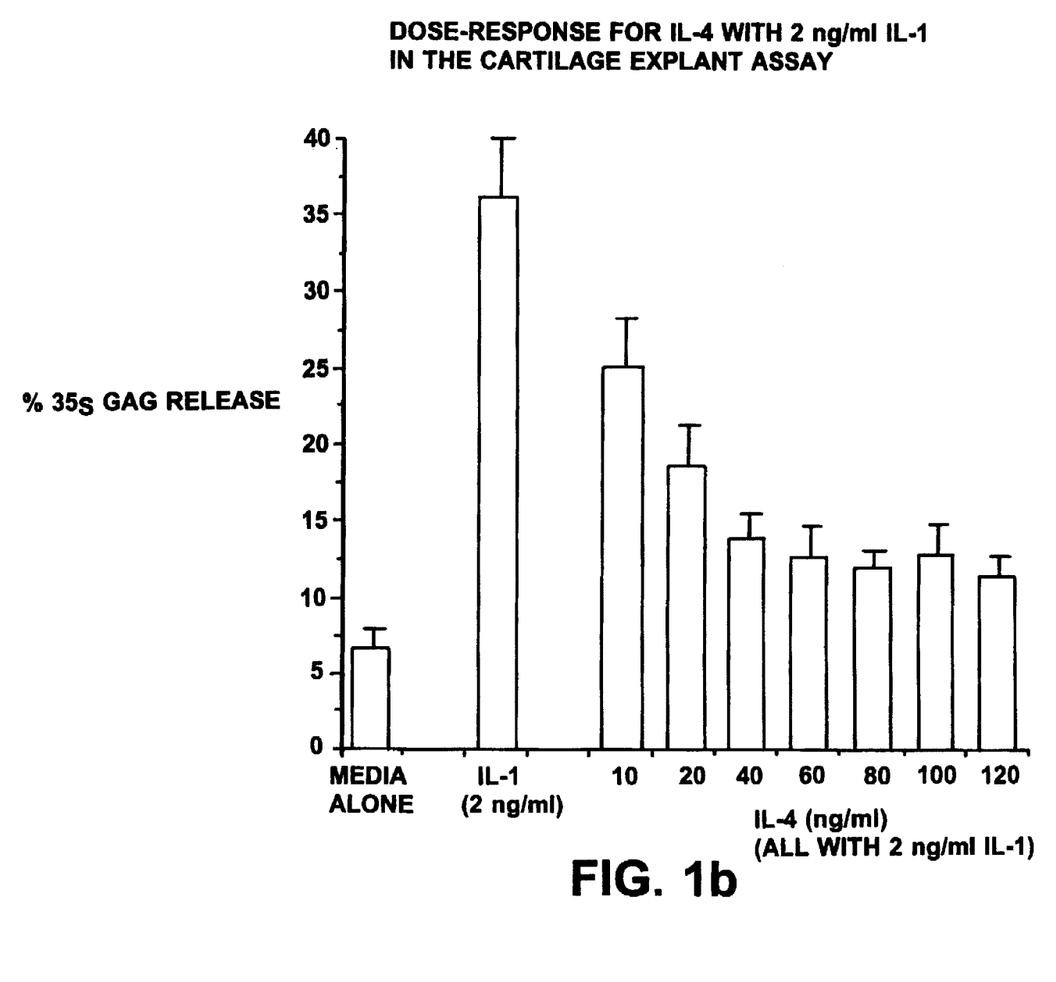
FIG. 1b describes the IL-4 inhibition of cartilage breakdown in a dose-dependent manner with an $IC_{50}$ of 10–20 ng/ml.
Figure 2A:
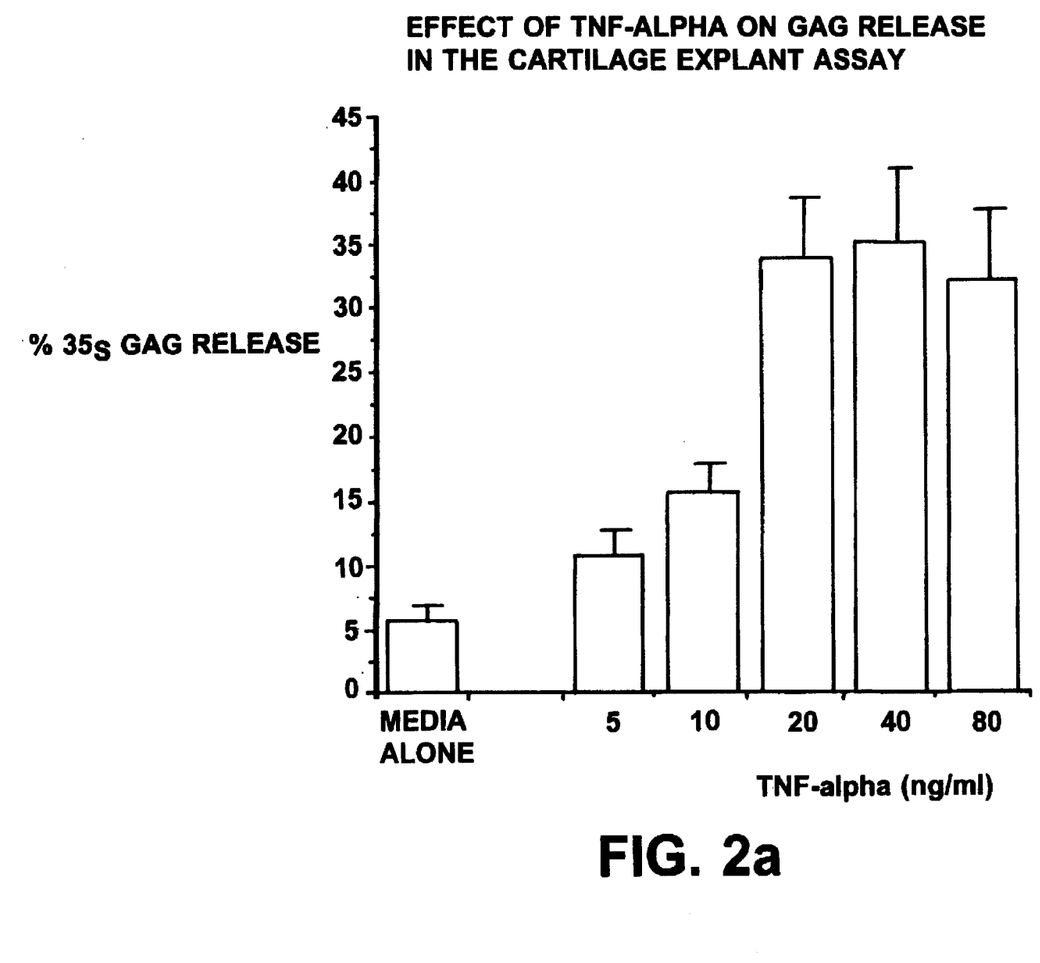
FIG. 2a describes the TNF-α-increased PG breakdown in the cartilage explant system.
Figure 2B:
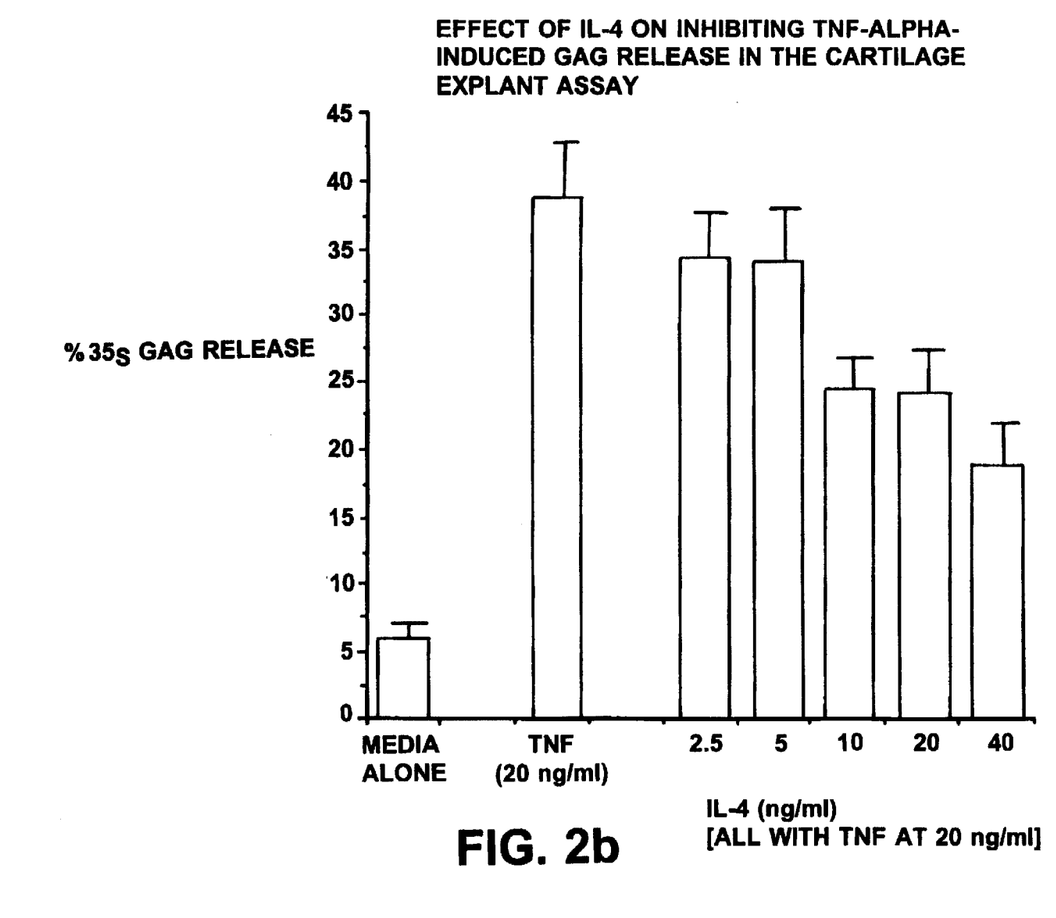
FIG. 2b describes the IL-4 inhibition of cartilage breakdown in a dose-dependent manner with an $IC_{50}$ of 10–20 ng/ml.
Figure 3:
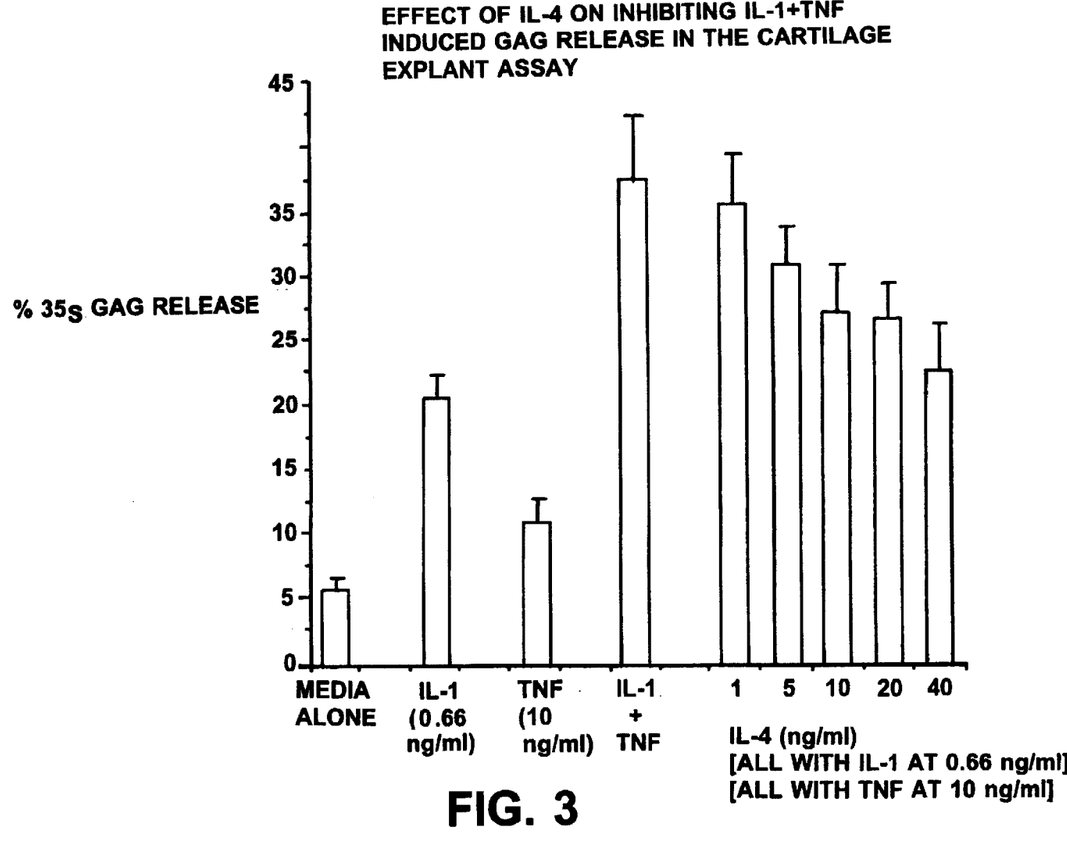
FIG. 3 describes that IL-1 and TNF-α in combination increased PG degradation in the cartilage explant system. The addition of increasing concentration of IL-4 decreased the PG breakdown with an $IC_{50}$ of 20–40 ng/ml.

Throughout the figures GAG (glycosaminoglycan) release is representative of PG release by the articular cartilage explants. FIG. 1a shows that increasing amounts of IL-1 in a bovine cartilage explant assay breaks down the PGs in the cartilage. FIG. 1b shows that as IL-4 is added to the assay, the release of GAG is minimized. FIG. 2a shows that TNF-α has a similar effect on producing GAG release which is indicative of PG breakdown. Along the same lines, as shown in FIG. 2b, when IL-4 is added to a TNF-α induced cartilage explant assay, the GAG release is minimized. FIG. 3 is representative of the synergistic effect of proteoglycan breakdown by IL-1 and TNF-α together. Again, the addition of IL-4 slows the GAG release in this assay.

Figure 4:
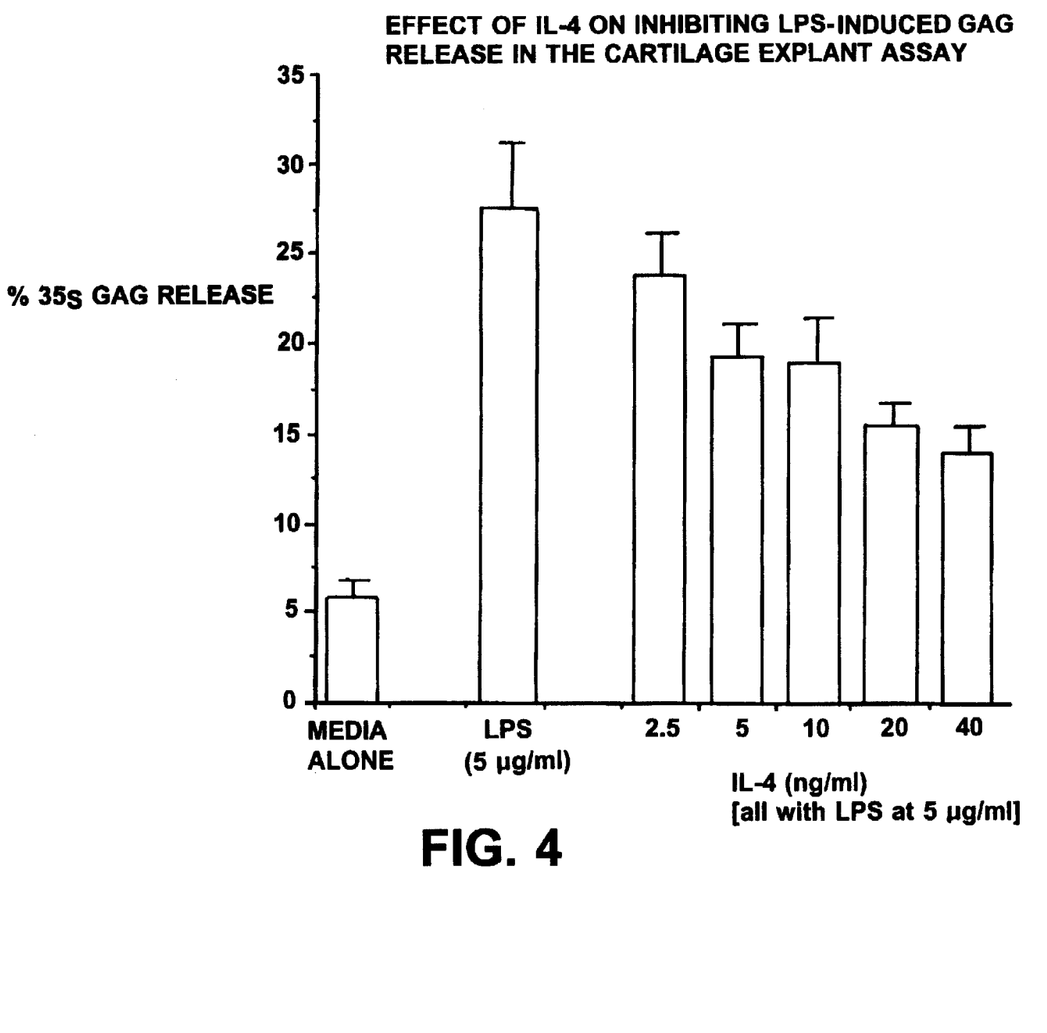
FIG. 4 describes LPS-stimulated PG breakdown in the articular cartilage explant system. The addition of IL-4 decreased the LPS-stimulated PG breakdown with an $IC_{50}$ of 20 ng/ml.

FIG. 4 shows the ability of LPS to break down PG in cartilage and that the addition of IL-4 minimizes this release.

Figure 5:
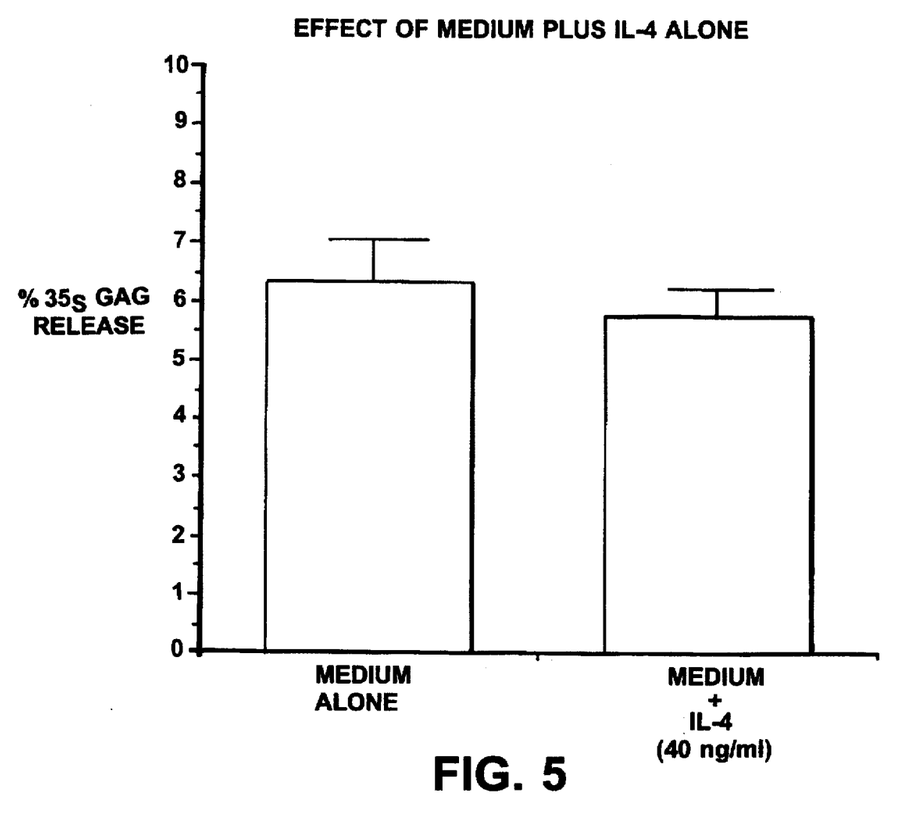
FIG. 5 describes IL-4 had no effect on basal level of PG turnover.

FIG. 5 shows that IL-4 itself has no effect on normal cartilage turnover, and that IL-4 only acts to decrease the collagen and PG breakdown in articular cartilage in a disease state, for example, osteoarthritis. This is significant since IL-4 is shown to act directly on IL-1, TNF-α and LPS in inhibiting articular cartilage breakdown, and that IL-4 itself has no effect on articular cartilage.

To analyze the inhibitory effect of IL-4 on cartilage PG in a more detailed manner, samples of concentrated media from the radiolabelled explant studies were subjected to acrylamide/agarose composite gel electrophoresis. In this procedure, the intensity of stained PG bands in gels is directly proportional to the amount of PG present in the sample (e.g., released into the medium). Additionally, different proteoglycan species migrate to different positions in the gel, for example, smaller PGs or PG fragments may migrate lower in the gel.

The electrophoretic data are highly consistent with the radiolabelled cartilage explant data. In the absence of IL-4, higher amounts of PGs are released into the media from IL-1, TNF-α and LPS treated explants compared with non-stimulated explants. Also consistent is the synergistic effect of the combination of IL-1 and TNF-α on PG release. The important observation from these gels is that it is apparent that treatment with IL-4 decreases the amount of PG released into the media from the cartilage explant. IL-4 also produces an altered electrophoretic pattern compared with non-IL-4-treated samples, with the major effect being a slight decrease in the mobility of the PG bands, i.e., when treated with IL-4 the PGs do not migrate as far as when not treated with IL-4 because they are not broken down into smaller fragments.

In accordance with a further aspect of the present invention there is provided a composition for reducing or inhibiting collagen and PG breakdown in articular cartilage, which leads to osteoarthritis, which comprises a therapeutically effective amount of IL-4 for reducing or inhibiting collagen and PG breakdown in articular cartilage, the composition may also include one or more pharmaceutically acceptable carriers.

The breakdown of collagen and PG by IL-1, TNF-α, and LPS alone, and the combination of IL-1 and TNF-α has been theorized to lead to other conditions such as tumor metastases, emphysema, osteoporosis and periodontal disease.

Accordingly the present invention also provides compositions and methods for treating metastatic tumors, which comprise administering a therapeutically effective amount of IL-4 to reduce or inhibit collagen and proteoglycan breakdown, optionally in the presence of a pharmaceutically acceptable carrier, to a patient in need of such treatment. Tumors metastasize from their organ of origin to other areas of the body by breaking down the collagen in the cellular matrix. This breakdown is due to the action of metalloproteinases. IL-4 suppresses the action of IL-1 and TNF-α and, therefore, the production and release of metalloproteinases is not stimulated. Therefore, tumors are prevented from metastasizing.

In accordance with another aspect of the present invention there is provided a composition and method for treating emphysema, which comprises administering to a subject a therapeutically effective amount of IL-4 to reduce or inhibit collagen and PG breakdown, optionally in the presence of a pharmaceutically acceptable carrier, to a patient in need of such treatment. Emphysema is characterized by low elasticity of the lung due to enzymatic degradation of collagen which makes it difficult to respire. Accordingly, administration of the compositions of the present invention prevent the degradation of collagen in the lung and the further progression of emphysema.

In accordance with yet a further aspect of the present invention, there is provided a composition and method for treating bone diseases such as osteoporosis and periodontal disease, which comprises administering to a subject a therapeutically effective amount of IL-4 to reduce or inhibit collagen and PG breakdown in bone tissue, optionally in the presence of a pharmaceutically acceptable carrier. By inhibiting collagen and PG breakdown in bone, bone resorption is slowed, and osteoporosis can be prevented. Further, the gums of the mouth (periodontal tissue) contain collagen which functions as connective tissue. Accordingly, since IL-4 can reduce or inhibit the breakdown of collagen, IL-4 may have applications in the treatment of periodontal disease.

IL-4 may also be employed in accordance with the present invention by the expression of IL-4 in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The pharmaceutical compositions may be administered in a convenient manner such as by the oral, intravenous, intraperitoneal, intramuscular, subcutaneous, intranasal or intradermal routes. The composition also may be administered to a human or animal subject by continuous infusion over a predetermined time period, for example for 10 minutes to 24 hours. Administration may be by way of an intravenous catheter connected to an appropriate pump, or by gravity feed. Administration is preferably local, but could be used systemically.

The amounts and dosage regimens of IL-4 administered to a subject will depend on a number of factors such as the mode of administration, the nature of the condition being treated, the body weight of the subject being treated and the judgment of the prescribing physician or veterinarian. Generally speaking, IL-4 may be administered in an amount of at least 8 µg/kg body weight and in most cases will not be administered in excess of about 0.8 mg/kg body weight per day. Preferably, the dosage is at least about 8 µg/kg body weight and usually need not be more than about 0.8 mg/kg body weight.

The quantity of the IL-4 and pharmaceutical carrier in a unit dosage such as a table capsule may vary from about 8 µg/kg body weight to about 0.8 mg/kg body weight of the subject. IL-4 may be coated by, or administered with, a material to prevent its inactivation. For example, the active material may be administered in an adjuvant co-administered with enzyme inhibitors or in liposomes. Adjuvants contemplated herein include resorcinol, nonionic surfactants such as polyoxyethylene oleyl esther and n-hexadecyl polyethylene ether. Enzyme inhibitors include pancreatic trypsin inhibitor, hydroxamate and trasylol. Liposomes include water-in-oil-in-water emulsions as well as conventional liposomes.

The pharmaceutical forms suitable for injectable use includes sterile aqueous solutions (where water soluble) or dispersions and sterile powders for the preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, sterile water, ethanol, polyol, suitable mixtures thereof, and vegetable oils. The proper fluidity can be maintained, for example, by the use of a coating such as a lecithin, by the maintenance of the required particle size in the case of a dispersion and the use of surfactants. The preventions of the actions of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active material in the required amount, in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When IL-4 is suitably protected as described above, the active compound may be orally administered, for example, with an inner diluent or with an edible carrier, or it may be enclosed in hard or soft shell gelatine capsules, or it may be compressed into tablets or it may be incorporated directly with the food of the diet. For oral therapeutic administration, the active material may be incorporated with excipients and used in the form of ingestible tablets, buccal, troches, capsules, elixirs, suspensions, syrups, wafers and the like.

As used herein, the terms pharmaceutically acceptable carrier and excipient include any and all solvents dispersion media, coatings, antibacterial and antifungal agents, isotonic and absorption delaying agents, and the like. The use of such carriers and excipients is well known in the art. Other examples of pharmaceutically acceptable carriers and excipients are saline, buffered saline, dextrose, water, glycerol, ethanol and combinations thereof. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ameliorate any pain at the site of injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

The therapeutic formulations of the invention may also be formulated as neutral or salt forms. Pharmaceutically acceptable salts include those formed with free amino groups, such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethyl amino ethanol, histamine, procaine, etc.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration.

The present invention will be further described with reference to the following examples, however, it needs to be understood that the present invention is not limited to such examples. All parts or amounts, unless otherwise specified, are by weight.

EXAMPLE 1

Effects of increasing IL-4 concentration on IL-1 and TNF-α

Bovine radiocarpal joints were obtained from a local slaughter house. Articular cartilage was cut into 3.5×1.0 mm disks and labeled with $^{35}$S-sodium sulfate (10 μCi/ml) in DMEM for 48 hours. The disks were then re-equilibrated with Dulbecco's modified Eagle medium (DMEM) without labeling for 24 hours. Recombinant human IL-1α, TNF-α, TNF-α plus IL-1α, or LPS with various concentrations of IL-4 were added to the cartilage disks and incubated at 37° C. with 5% $CO_2$ and 95% air for 3 days. Portions of the supernatant were counted by a scintillation counter. The cartilage disks were dissolved in formic acid and heated at 70° C. for 6 hours. Portions of the formic acid digest were also counted by a scintillation counter. The percentage of $^{35}$S release into the media was calculated. This release of $^{35}$S-GAG is representative of the proteoglycan pool in the extracellular matrix of cartilage, and reflects PG degradation. See FIG. 1a.

As shown in FIG. 1a, in the presence of increasing amounts of human recombinant IL-1α at 0.5, 1.0, 1.5 and 2.0 ng/ml there is an increase in $^{35}$S-GAG release into the culture media. When various concentrations of IL-4 are added to cartilage explants along with a fixed amount of IL-1 (2 ng/ml) (see FIG. 1b), the % $^{35}$S-GAG release is decreased compared with IL-1 alone. The inhibition by IL-4 of $^{35}$S-GAG release is dose-dependent and has an $IC_{50}$ of 10–20 ng/ml.

EXAMPLE 2

Effects of increasing IL-4 concentration on TNF-α-stimulated $^{35}$S-GAG release The ability of IL-4 to inhibit breakdown of the proteoglycan matrix of cartilage was assessed by the methods described in example 1. As illustrated in FIG. 2a, in the presence of increasing amounts of human recombinant TNF-α at 5, 10, 20, 40 and 80 ng/ml, there is an increase in $^{35}$S-GAG release into the media. When various concentrations of IL-4 are added to the explant along with TNF-α (20 ng/ml) (see FIG. 2b), the % $^{35}$S-GAG release decreased compared with TNF-α alone. The inhibition by IL-4 of $^{35}$S-GAG release is dose-dependent and has an $IC_{50}$ of 10–20 ng/ml.

EXAMPLE 3

Effects of increasing IL-4 concentration on IL-1 and TNF-α-stimulated $^{35}$S-GAG release The ability of IL-4 to inhibit breakdown of the proteoglycan matrix of cartilage was assessed by the methods described in example 1. As illustrated in FIG. 3, in the presence of both IL-1 (0.66 ng/ml) and TNF-α (10 ng/ml), the degradation of PG is much enhanced, as demonstrated by the release of $^{35}$S-GAG into the media. However, the addition of various concentrations of IL-4 (1–40 ng/ml final concentration) decreased the breakdown of the proteoglycan matrix of cartilage with an $IC_{50}$ of 20–40 ng/ml.

EXAMPLE 4

Effects of increasing IL-4 concentration on LPS-stimulated $^{35}$S-GAG release in the explant assay The ability of IL-4 to inhibit the breakdown of the proteoglycan matrix of cartilage was assessed by the methods described in example 1. As illustrated in FIG. 4, LPS at 5 μg/ml stimulated the release of $^{35}$S-GAG into the media.

The addition of increasing concentrations of IL-4 (2.5, 5, 10, 20 and 40 ng/ml) decreased the breakdown of the proteoglycan matrix of cartilage with an $IC_{50}$ of 20 ng/ml.

EXAMPLE 5

Effects of IL-4 on basal level of cartilage turnover

IL-4 had no effect on the unstimulated $^{35}$S-GAG release as illustrated in FIG. 5. This was assessed by the methods described in example 1. The only addition to the cartilage was vehicle control (DMEM). This result indicated that IL-4 has no adverse effect on cartilage turnover under normal condition.

EXAMPLE 6

Composite agarose/acrylamide gel electrophoresis of media from IL-1, TNF-α, and LPS stimulated bovine articular explants Agarose/acrylamide composite gels electrophoresis and staining of PGs with toluidine blue dye were performed by the method of Varelas, et al., Anal. Biochem., 197:396–400 (1991), with the following modification: final concentrations of 0.6% agarose/1.2% acrylamide were used instead of 1.2% agarose/1.2% acrylamide. The samples used for this experiment were the samples of concentrated media from the radiolabelled explant studies from Example 1–5. See Examples.

Numerous modifications and variations of the present invention are possible in light of the above teachings and, therefore, within the scope of the appended claims, the invention may be practiced otherwise than as particularly described.

What is claimed is:

1. A method for inhibiting articular cartilage breakdown comprising:

administering to an animal in need thereof a therapeutically effective amount of IL-4 to inhibit articular cartilage breakdown.

2. A method of claim 1 wherein IL-4 is administered in an amount of between 8 µg/Kg body weight and 0.8 mg/kg body weight.

* * * * *